(12) United States Patent
Johnen et al.

(10) Patent No.: US 9,174,922 B2
(45) Date of Patent: Nov. 3, 2015

(54) METHOD FOR PRODUCING VINYL ESTERS

(71) Applicant: Oxea GmbH, Oberhausen (DE)

(72) Inventors: Leif Johnen, Voerge (DE); Heinz Strutz, Moers (DE); Kurt Schalapski, Oberhausen (DE); Norman Nowotny, Essen (DE); Wolfgang Höfs, Oberhausen (DE); Sebastian Geisel, Essen (DE)

(73) Assignee: OXEA GMBH, Oberhausen (DE)

( * ) Notice: Subject to any disclaimer, the term of this patent is extended or adjusted under 35 U.S.C. 154(b) by 0 days.

(21) Appl. No.: 14/372,290

(22) PCT Filed: Jan. 18, 2013

(86) PCT No.: PCT/EP2013/000141
§ 371 (c)(1),
(2) Date: Jul. 15, 2014

(87) PCT Pub. No.: WO2013/117294
PCT Pub. Date: Aug. 15, 2013

(65) Prior Publication Data
US 2014/0343310 A1   Nov. 20, 2014

(30) Foreign Application Priority Data
Feb. 6, 2012 (DE) .................. 10 2012 002 282

(51) Int. Cl.
| C07C 67/10 | (2006.01) |
| C07C 67/333 | (2006.01) |
| C07C 69/01 | (2006.01) |
| C07C 67/54 | (2006.01) |

(52) U.S. Cl.
CPC ............. *C07C 67/333* (2013.01); *C07C 67/10* (2013.01); *C07C 67/54* (2013.01); *C07C 69/01* (2013.01)

(58) Field of Classification Search
None
See application file for complete search history.

(56) References Cited

U.S. PATENT DOCUMENTS

| 2,245,131 A | 6/1941 | Herrmann et al. |
| 2,299,862 A | 10/1942 | Toussaint et al. |

(Continued)

FOREIGN PATENT DOCUMENTS

| DE | 1222493 B | 8/1966 |
| EP | 0054158 A1 | 6/1982 |

(Continued)

OTHER PUBLICATIONS

Ketterling, A.A., et al., Carbosylic acid transvinylatoin as catalysed by complexes of palladium aceate with phenanthroline-like ligands, 1990, Applied Catalysis, vol. 66, pp. 123-132.*

(Continued)

*Primary Examiner* — Yate K Cutliff
(74) *Attorney, Agent, or Firm* — Michael W. Ferrell

(57) ABSTRACT

The present invention relates to a continuous, catalytic process for preparing a vinyl ester of the formula R—C(O)O—CH=CH$_2$ by reaction of a carboxylic acid of the formula R—C(O)OH with a transvinylating reagent of the formula R$^1$—C(O)O—CH=CH$_2$, wherein the reaction is effected at a temperature of 90 to 160° C. and at a pressure of 0.5 to 15 MPa without withdrawal of a reactant in the presence of a transition metal catalyst containing at least one transition metal from the group of ruthenium, osmium, rhodium, iridium, palladium and platinum, and then the resulting reaction mixture is separated into its constituents.

19 Claims, 1 Drawing Sheet

(56) References Cited

U.S. PATENT DOCUMENTS

| | | | |
|---|---|---|---|
| 2,997,495 A * | 8/1961 | Rutledge et al. | 554/165 |
| 4,425,277 A | 1/1984 | Kawamoto et al. | |
| 4,981,973 A * | 1/1991 | Murray | 548/229 |
| 5,210,207 A * | 5/1993 | Mokhtarzadeh et al. | 548/239 |
| 5,214,172 A * | 5/1993 | Waller | 554/165 |
| 5,223,621 A | 6/1993 | Vallejos et al. | |
| 5,741,925 A | 4/1998 | Mao et al. | |
| 2004/0147757 A1 | 7/2004 | Takai et al. | |
| 2011/0275853 A1 * | 11/2011 | Kotsianis et al. | 560/234 |

FOREIGN PATENT DOCUMENTS

| | | |
|---|---|---|
| EP | 0351603 A2 | 1/1990 |
| EP | 0376075 A2 | 7/1990 |
| EP | 0497340 A2 | 8/1992 |
| EP | 0506070 A2 | 9/1992 |
| EP | 1057525 A2 | 12/2000 |
| JP | 2002-322125 A | 11/2002 |
| WO | 9209554 A1 | 6/1992 |
| WO | 2011139360 A1 | 11/2011 |
| WO | 2011139361 A1 | 11/2011 |

OTHER PUBLICATIONS

International Preliminary Report on Patentability dated Aug. 7, 2014.
International Search Report dated Apr. 16, 2013.
Ullmanns Encyklopädie der technischen Chemie, 4th edition, 1975, pp. 143-145, vol. 9, Verlag Chemie, Weinheim/Bergstr.
G. Hübner, "Vinylierung höherer Carbonsäuren an Katalysatorschmelzen", Fette, Seifen, Anstrichmittel, 1966, pp. 290-292, 68-4.
Ullmanns Encyklopädie der technischen Chemie, 4th edition, 1983, pp. 606-607, vol. 23, Verlag Chemie, Weinheim.
Adelman, "The Interchange Reaction of Vinyl Acetate with Organic Acids", Journal of Organic Chemistry, 1949, pp. 1057-1077, 14.
Murray et al., "New Catalytic Route to Vinyl Esters", Catalysis Today, 1992, pp. 93-102, 13, Elsevier Science Publishers B.V., Amsterdam.

* cited by examiner

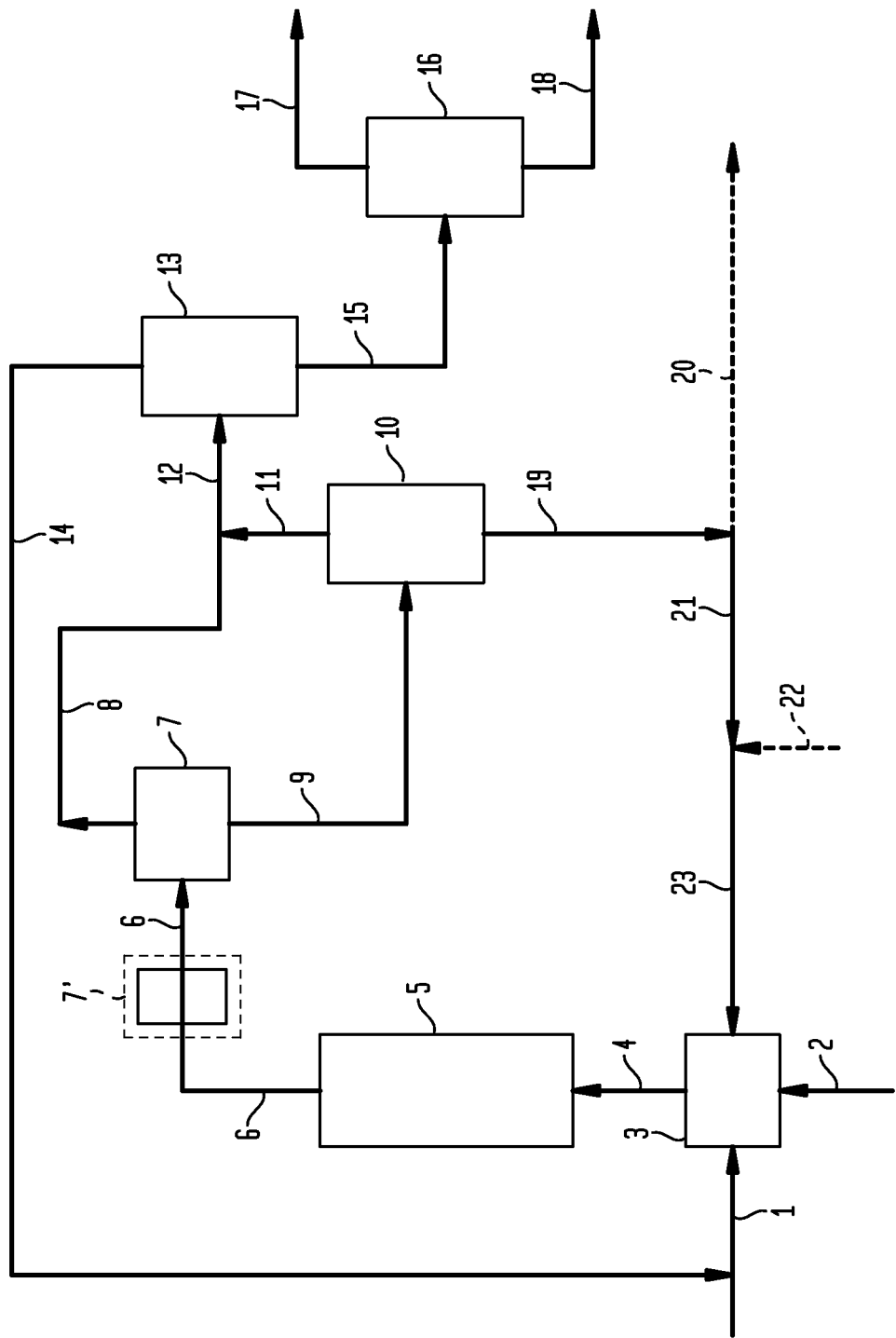

METHOD FOR PRODUCING VINYL ESTERS

CLAIM FOR PRIORITY

This application is a national phase application of PCT/EP2013/000141 FILED Jan. 18, 2013 which was based on application DE 10 2012 002 282.4 FILED Feb. 6, 2012. The priorities of PCT/EP2013/000141 and DE 10 2012 002 282.4 are hereby claimed and their disclosures incorporated herein by reference.

TECHNICAL FIELD

The present invention relates to a catalytic process for the continuous preparation of a vinyl ester of a carboxylic acid by the transvinylation reaction of a vinyl ester of another carboxylic acid.

BACKGROUND

Vinyl esters of higher carboxylic acids are of certain economic significance as comonomers. They can be used to modify the properties of polymers, for example polyvinyl chloride, polyvinyl acetate, polystyrene or polyacrylic esters. For example, the hydrolysis resistance of emulsion paints can be increased. For the production of adhesives too, vinyl esters of higher carboxylic acids are used. For these fields of use, vinyl esters based on 2-ethylhexanoic acid, isononanoic acid, lauric acid or the Versatic Acids 911, 10 and 1519 from Shell have been found to be of industrial significance. These higher carboxylic acids are obtainable, for example, by oxidation of aldehydes which have been prepared by the oxo reaction, or by the Koch synthesis from the olefin, carbon monoxide and water. In the case of vinyl esters based on 2-ethylhexanoic acid, lauric acid or isononanoic acid, if the isononanoic acid consists predominantly of 3,5,5-trimethylhexanoic acid, the compounds are homogeneous, whereas, in the case of vinyl esters of the Versatic Acids 911, mixtures of highly branched carboxylic acids having 9 to 11 carbon atoms are bound within the vinyl ester, and, in the case of vinyl esters of the Versatic Acids 1519, mixtures of highly branched carboxylic acids having 15 to 19 carbon atoms. In the case of vinyl esters of Versatic Acid 10, highly branched decanoic acids of differing structure, such as neodecanoic acids, are derivatized. 3,5,5-Trimethylhexanoic acid is prepared on the in scale by hydroformylation of diisobutylene and subsequent oxidation or the corresponding aldehyde (Ullmanns Encyklopädie der technischen Chemie, $4^{th}$ edition, 1983, Verlag Chemie, Volume 9, pages 143-145; Volume 23, pages 608-607).

It is known that vinyl esters of carboxylic acids earn be prepared by reaction of acetylene with carboxylic acids (G. Hübner, Fette, Seifen, Anstrichmittel 68, 290 (1966) Ullmanns Encyklopädie der technischen Chemie, $4^{th}$ edition, 1983; Verlag Chemie, Volume 23, pages 606-607). This procedure is adopted in EP 1 057 525 A2, according to which gaseous acetylene is reacted with the carboxylic acid to be vinylated in the presence of a catalyst in a tubular reactor. In the known multiphase process, the carboxylic acid comprising the catalyst, for example a zinc salt, in dissolved form constitutes the continuous phase in which gaseous acetylene is present as a dispersed phase. The tubular reactor is operated at a load factor of greater than 0.8. The use of acetylene as a raw material on the industrial scale, however, requires a high level of apparatus and safety complexity, and acetylene is additionally generally available only locally.

It is likewise known that the vinyl esters of carboxylic acids can be prepared by what is called the transvinylation reaction with a vinyl ester of another carboxylic acid;

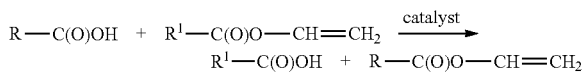

where R and $R^1$ may each be an aliphatic or aromatic radical. In order to control the equilibrium reaction in the direction of the products, a high excess of the transvinylating reagent $R^1$—C(O)O—CH=CH$_2$ is frequently used. The carboxylic acid $R^1$—C(O)OH formed should also be of sufficient volatility to be withdrawn rapidly from the equilibrium and hence to generate an elevated conversion. Since the reaction mixture is generally worked up by distillation, the choice of transvinylating reagent $R^1$—C(O)O—CH=CH$_2$ is frequently guided by the boiling points of the other reaction participants (Ullmanns Encyklopädie der technischen Chemie, $4^{th}$ edition, 1983, Verlag Chemie, Volume 23, pages 606-607). For the preparation of vinyl esters of higher carboxylic acids, vinyl acetate in particular and vinyl propionate to a certain extent are suitable as transvinylating reagents. Vinyl acetate, being a chemical produced on the industrial scale, is available inexpensively. Vinyl acetate and the acetic acid formed therefrom have comparatively low boiling points and can be separated by distillation from the desired vinyl ester of the higher carboxylic acid.

There are numerous hints in the literature regarding the transvinylation reaction of carboxylic acids with vinyl acetate as the vinylating reagent. Adelman, Journal of Organic Chemistry, 1949, 14, pages 1057-1077 studies the transvinylation of higher carboxylic acids, such as stearic acid, lauric acid or 3,5,5-trimethylhexanoic acid, with vinyl acetate in the presence of mercury salts as a catalyst. U.S. Pat. No. 2,245,131 discusses the reaction of benzoic acid or crotonic acid with vinyl acetate in the presence of mercury acetate. The reaction mixture is at first kept under reflux. Subsequently, the reaction temperature is increased and the acetic acid formed is removed. The vinyl benzoate formed is then purified in a further fractional distillation. U.S. Pat. No. 2,299,862 discloses the preparation of vinyl 2-ethylhexanoate proceeding from 2-ethylhexanoic acid and vinyl acetate in the presence of mercury acetate and sulphuric acid. The resulting crude mixture is first neutralized with sodium acetate and then distilled. Vinyl 2-ethylhexanoate is obtained with a yield of 73%. According to DE 1222493 B, the catalyst used for the transvinylation with vinyl acetate are mercury salts of a sulphonic acid cation exchange resin.

Disadvantages of the transvinylation processes with mercury catalysts are the toxicity and volatility thereof, and the unwanted formation of ethylidene diesters. The activation, typically with sulphuric acid, and the need to deactivate the catalyst prior to the distillation of the reaction mixture by neutralization also mean additional process steps.

These disadvantages can be avoided by the use of palladium catalysts, in the case of which the modification of the palladium complexes with aromatic nitrogen ligands, for example with 2,2'-bipyridyl or 1,10-phenanthroline, has been found to be advantageous. According to U.S. Pat. No. 5,214,172, the activity of palladium catalysts modified in this way is increased by the addition of strong acids. U.S. Pat. No. 5,741,925 discusses the transvinylation of naphthenic acids in the presence of palladium complexes modified with 2,2'-bipyridyl or 1,10-phenanthroline. In accordance with the known procedure, naphthenic acids, preferably cyclic $C_{10}$-$C_{20}$ carboxylic acids, are converted to the corresponding vinyl esters with vinyl acetate as the transvinylating reagent under reflux. The catalyst is stable during the distillation and can be reused in several runs. The process disclosed according to U.S. Pat. No. 5,223,621 relates to the transvinylation of carboxylic acids, for example of lauric acid or benzoic acid, with a (2,2'-bipyridyl)palladium(II) diacetate complex formed in situ under reflux. Prior to the distillation of the crude product, the catalyst is precipitated with oxalic acid or hydrochloric acid and filtered off.

The use of a combined catalyst system composed of a palladium salt and a redox agent for transvinylation of carboxylic acids is also known. EP 0 376 075 A2 recommends a redox-active catalyst system composed of palladium chloride, copper(II) bromide and lithium acetate. By way of example, the batchwise transvinylation of lauric acid with vinyl acetate close to the boiling point of vinyl acetate is described. The desired vinyl ester is obtained in pure form in a subsequent distillation. A further configuration of a redox-active catalyst system is disclosed in JP 2002-322125 A. This involves heating the reaction mixture composed of carboxylic acid and vinyl acetate, and also palladium acetate and lithium acetate, to 65° C.

Likewise mentioned in the prior art is the use of ruthenium catalysts for the transvinylation reaction. According to Murray, Catalysis Today 1992, 13, pages 93-102, higher carboxylic acids such as 2-ethylhexanoic acid, benzoic acid, neodecanoic acid, neononanoic acid or adipic acid can be converted to the corresponding vinyl esters with vinyl acetate in the presence of metallic ruthenium or ruthenium compounds such as ruthenium chloride, ruthenium oxide or ruthenium carbonyls such as $Ru_3(CO)_{12}$. This reaction is conducted batchwise under carbon monoxide or nitrogen at a pressure of about 2 bar and a temperature of typically 130 to 150° C. A corresponding process is likewise known from EP 0 351 603 A2 and EP 0 506 070 A2. It is pointed out that ruthenium catalysts are more thermally stable than palladium catalysts, which are deactivated at elevated temperatures with deposition of metallic palladium. However, in the case of the known ruthenium-catalysed processes, only moderate yields are reported.

The majority of the transvinylation reaction processes described in the prior art are conducted batchwise, usually under reflux and occasionally under pressure in a closed reaction vessel.

A continuously operated transvinylation process is known from EP 0 497 340 A2. By means of a continuously operated reactive distillation, by continuous removal of the most volatile reaction component, the equilibrium of the transvinylation reaction R—C(O)OH+$R^1$—C(O)O—CH=$CH_2$→$R^1$—C(O)OH+R—C(O)O—CH=$CH_2$ is shifted in the direction of the products. The transvinylating reagent $R^1$—C(O)O—CH=$CH_2$ is chosen such that the corresponding acid $R^1$—C(O)OH is volatile and is removed from the equilibrium. The process according to EP 0 497 340 A2 uses preferably vinyl acetate as the transvinylating reagent, and the acetic acid formed is removed from the reaction zone together with unreacted vinyl acetate. Subsequently, the vinyl acetate separated from the acetic acid in a separate step is returned back to the reaction zone. The known process works with ruthenium catalysts, for example with [$Ru(CO)_2OAc$]$_n$, and describes the transvinylation of adipic acid, neodecanoic acid and 2-ethylhexanoic acid. In order, however, to suppress the unwanted formation of acid anhydrides, it is run only up to a partial conversion of the desired vinyl ester.

WO 2011/139360 A1 and WO 2011/139361 A1 disclose a continuous and semicontinuous transvinylation process for carboxylic acids with vinyl acetate, using palladium complexes containing aromatic nitrogen ligands such as 2,2'-bipyridyl and 1,10-phenanthroline. The continuous process is operated in a bubble column with attached packed column, downstream of which may additionally be connected a rectification column and a stripping column. Vinyl acetate is introduced into the bubble column while, at the same time, a mixture of the carboxylic acid and vinyl acetate containing the catalyst in dissolved form is introduced into the attached packed column. Carboxylic acid and catalyst flow into the bubble column, while vinyl acetate is conducted through the bubble column and through the attached packed column in countercurrent. Vinyl acetate and acetic acid formed are removed and separated in a downstream rectification column and stripping column.

WO92/09554 A1 discloses a process for preparing vinyl esters in the presence of ruthenium catalysts, wherein the reaction mixture obtained is worked up using an azeotroping agent. The process can be performed continuously, semi-continuously, batchwise or semi-batchwise.

U.S. Pat. No. 4,425,277 discloses a continuous process for preparing vinyl esters. The reaction is effected in the presence of a supported palladium catalyst with an added cocatalyst composed of an alkali metal compound and a copper(II) compound.

EP 0 054 158 A1 likewise relates to a continuous process for preparing vinyl esters. The reaction is effected in the presence of a supported catalyst based on palladium(II) salts having activated carbon as a support material with a particular analytical $SiO_2$ content.

A disadvantage of the continuous processes described in the prior art is that the transvinylating reagent vinyl acetate is not utilized efficiently for preparation of the vinyl ester because it vaporizes after a very short residence time due to the reaction conditions selected and is no longer available to the transvinylation reaction as a result. Moreover, the known continuously operated transvinylation processes are complex in terms of apparatus and have to be designed with high capital costs, since a series of columns have to be connected downstream of the reaction vessel, these working as additional reaction columns. The known processes therefore allow only moderate space-time yields of the desired vinyl ester.

There is therefore a need for a continuously operated process for transvinylation of carboxylic acids which is easy to perform having a low level of apparatus complexity and enables a high space-time yield, i.e. a high product output per unit reaction volume and time, of the desired vinyl ester. The desired vinyl ester is likewise to be obtained with a high selectivity.

SUMMARY OF INVENTION

The present invention therefore consists in a continuous, catalytic process for preparing a vinyl ester of the formula R—C(O)O—CH=$CH_2$ by reacting a carboxylic acid of the formula R—C(O)OH with a transvinylating reagent of the formula $R^1$—C(O)O—CH=$CH_2$ where R and $R^1$ are each independently an aliphatic, cycloaliphatic or aromatic radical, characterized in that the reaction is effected at a temperature of 90 to 160° C. and at a pressure of 0.5 to 15 MPa without withdrawal of a reactant in the presence of a transition metal catalyst containing at least one transition metal selected from the group of ruthenium, osmium, rhodium, iridium, palladium and platinum, and then the resulting reaction mixture is separated into its constituents.

In contrast to the known continuously operated processes, in which at least one reactant is continuously withdrawn from the transvinylation equilibrium and hence the chemical equilibrium is constantly disturbed, the reaction in the process according to the invention is conducted without withdrawal of a reactant in the steady state. The reaction system is in the steady state and the mixture withdrawn from the reaction vessel is not separated into its constituents until the subsequent workup. The reaction of the carboxylic acid R—C(O)OH with the transvinylating reagent $R^1$—C(O)O—CH=$CH_2$ is effected in the presence of a transition metal catalyst and is performed at temperatures of 90 to 160° C., preferably of 90 to 150° C. and especially of 90 to 140° C. Even though the process according to the invention is operated without withdrawal of a reactant, it is nevertheless surprisingly possible to achieve a high yield and a high space-time yield of the desired vinyl ester.

BRIEF DESCRIPTION OF DRAWING

The invention is described in detail below with reference to the single FIGURE which is a schematic diagram illustrating the process and an illustrative system for practicing the present invention.

DETAILED DESCRIPTION

The transvinylation reaction is conducted at a pressure of 0.5 to 15 MPa, preferably of 0.5 to 8 MPa and especially of 0.8 to 2 MPa. Very particularly suitable reaction settings have been found to be a temperature of 90 to 140° C. and a pressure of 0.8 to 2 MPa. However, even at standard pressure and especially at a reaction temperature of 90 to 150° C., likewise very high space-time yields of the desired vinyl esters are achieved.

A suitable reaction vessel is a tubular reactor, such as a flow tube in any arrangement, for example a vertical or horizontal flow tube or a multiply coiled flow tube. The tubular reactor may be operated as an empty tube, but it may likewise contain random packings or internals, for example Raschig rings, saddles, Pall rings, spirals, baffles or static mixers or mixer packings. Static mixing elements are commercially available and are supplied, for example, as Sulzer mixers or Kenicks mixers with specific product lines for the mixing of liquids of different viscosity. The tubular reactor may likewise be provided with a circulation pump and optionally with a heat exchanger.

In the course of operation of the tubular reactor, the starting carboxylic acid R—C(O)OH and the transvinylating reagent $R^1$—C(O)O—CH=$CH_2$ can be introduced into the tubular reactor separately but simultaneously, in countercurrent or cocurrent. It is also possible to mix the two liquids beforehand and to introduce them to the tubular reactor as a homogeneous solution. In a particular embodiment, the homogeneous solution is conducted through an upstream static mixing element prior to entry into the tubular reactor.

The transvinylation reaction can likewise be conducted continuously in a stirred tank or in a stirred tank cascade under pressure. The starting carboxylic acid R—C(O)OH and the transvinylating reagent $R^1$—C(O)O—CH=$CH_2$ are fed in continuously, either separately or as a mixture, and the reaction mixture in the steady state is removed continuously. Likewise possible is continuous conduct of the reaction in reactor designs customary in the art, such as in a loop reactor with utilization of thermal convection, or a multichamber reactor. The reaction vessel may likewise be configured as a cylindrical reactor with an axially arranged nozzle for the admission of the liquid, catalyst-containing mixture of the starting carboxylic acid R—C(O)OH and the transvinylating reagent $R^1$—C(O)O—CH=$CH_2$, which additionally also contains an axially arranged guide tube for generation of an internal forced flow.

An advantageous reaction vessel space velocity V/Vh of a mixture of the transvinylating reagent and the starting carboxylic acid to be vinylated prepared beforehand has been found to be 0.4 to 7.0 $h^{-1}$, preferably 0.7 to 6.2 $h^{-1}$, based on the reactor volume and time. If the two reactants are introduced separately but simultaneously into the reaction vessel, the reaction vessel space velocity V/Vh of the transvinylating reagent is from 0.2 to 6.0 $h^{-1}$, and that of the starting carboxylic acid to be vinylated from 0.1 to 6.7 $h^{-1}$, based in each case on the reactor volume and time.

By virtue of the continuous process regime conducted in the steady state, it is advantageously possible to achieve very high space-time yields compared to the known reactive distillation, in which the carboxylic acid formed is continuously removed from the reaction system together with the transvinylating reagent. This process regime additionally entails a high input of the transvinylating reagent in order constantly to ensure a sufficiently high concentration in the reaction mixture and in order to give a sufficient loading of the reactive distillation column, and a high circulation rate for the transvinylating reagent is necessary. The known continuous reaction regime requires a high reactor volume and a high level of apparatus complexity.

Therefore, only moderate space-time yields are achieved with a comparatively high level of apparatus complexity, combined with high capital costs.

For avoidance of side reactions, such as the polymerization of the vinyl esters, a suitable inhibitor, such as hydroquinone, methoxyhydroquinone, tert-butylcatechol or phenothiazine, can be added to the transvinylating reagent prior to entry into the reaction vessel. However, it is also possible to introduce the inhibitor separately and continuously into the reaction vessel. The concentration of the inhibitor in the homogeneous reaction mixture is generally from 3 to 150 ppm, based on the amount of the transvinylating reagent used.

Suitable starting carboxylic acids R—C(O)OH which can be converted to the corresponding vinyl ester by the process according to the invention are aliphatic, cycloaliphatic or aromatic carboxylic acids. The organic R radical contains typically 2 to 20 carbon atoms, preferably 4 to 13. The aliphatic carboxylic acids include, for example, propionic acid, n-butyric acid, isobutyric acid, n-valeric acid, 2-methylbutyric acid, 3-methylbutyric acid, pivalic acid, n-heptanoic acid, 2-methylhexanoic acid, 2-ethylhexanoic acid, n-octanoic acid, n-nonanoic acid, isononanoic acid, neononanoic acid, n-decanoic acid, 2-propylheptanoic acid, neodecanoic acid or Versatic Acid 10, Versatic Acids 911, Versatic Acids 1519, lauric acid, tridecanoic acid, palmitic acid or stearic acid. Among the various isononanoic acids which can be transvinylated by the process according to the invention, 3,5,5-trimethylhexanoic acid should be mentioned, this being obtainable by hydroformylation of diisobutylene to the corresponding 3,5,5-trimethylhexanal and subsequent oxidation. If diisobutylene is reacted with carbon monoxide and water in the presence of strongly acidic catalysts, predominantly 2,2,4,4-tetramethylpentanoic acid is obtained, which is also referred to as neononanoic acid. Pivalic acid, neononanoic acid, neodecanoic acid or Versatic Acid 10, or the Versatic Acids 911, a mixture of isomeric C9 to C11 carboxylic acids, and Versatic Acids 1519, a mixture of isomeric C15 to C19 carboxylic acids, are highly branched carboxylic acids which bear three alkyl radicals on the carbon atom adjacent to the carboxyl group and have what is called a neo structure. In spite of the high branching close to the carboxyl group, these neo acids can be converted with very good yields to the corresponding vinyl esters. Versatic Acid is a Shell brand name.

In addition, it is also possible to convert aromatic carboxylic acids, such as benzoic acid or naphthalenecarboxylic acid, or unsaturated aliphatic carboxylic acids, such as acrylic acid, crotonic acid or methacrylic acid, to the vinyl derivative. Liquid carboxylic acids can be used directly in the process according to the invention. Solid carboxylic acids are dissolved in a solvent, for example in toluene, THF, dioxane or cyclic ethers, or directly in the transvinylating reagent, and used as a solution in the transvinylation reaction. Suitable transvinylating reagents $R^1C(O)O$—CH=CH$_2$ are all vinyl esters which are available inexpensively in large amounts on an industrial scale. In general, $R^1$ is an aliphatic, cycloaliphatic or aromatic radical. The organic radical $R^1$ contains typically 1 to 20 carbon atoms. Preference is given to using vinyl acetate where $R^1$ is methyl, or vinyl propionate where $R^1$ is ethyl, but also vinyl esters of higher carboxylic acids such as vinyl laurate where $R^1$ is undecyl. The choice of transvinylating reagent depends on the physical properties of the carboxylic acid R—C(O)OH to be derivatized and the reactants $R^1$—C(O)OH and R—C(O)O—CH=CH$_2$ formed, and is guided by the process by which the reaction mixture can appropriately be separated into the various components. Typically, the transvinylating reagent $R^1$—C(O)O—CH=CH$_2$ recovered and the starting carboxylic acid R—C(O)OH recovered are recycled back into the transvinylating reaction. The carboxylic acid $R^1$—C(O)OH formed by the transvinylating reaction is removed in the course of workup of the reaction mixture, and the desired vinyl ester R—C(O)O—CH=CH$_2$ is purified further. Typically, the resulting reaction mixture is worked up by distillation; workup by means of crystallization or precipitation is not ruled out, but is restricted to particular special cases.

It has been found to be appropriate, in the workup of the reaction mixture and in the further purification of the desired vinyl ester, likewise to add an inhibitor, such as hydroquinone, methoxyhydroquinone, tert-butylcatechol or phenothiazine. The transvinylation catalyst obtained in the workup of the reaction mixture is subsequently recycled back into the transvinylating reaction, optionally after addition of fresh catalyst or fresh ligands.

Based on the carboxylic acid input R—C(O)OH, the transvinylating reagent $R^1$—C(O)O—CH=CH$_2$ can be used in a molar ratio of 0.1:1 to 10:1, preferably of 0.2:1 to 5:1. The amount thereof is likewise guided by the physical properties of the feedstocks and the reactants formed, and the manner in which the reaction mixture can most advantageously be worked up.

Due to inexpensive availability, the boiling point thereof and the boiling point of the acetic acid formed in the transvinylating reaction, vinyl acetate has been found to be an advantageous transvinylating reagent, especially in the transvinylation of carboxylic acids having five or more carbon atoms, for example of n-valeric acid, 2-methylbutyric acid, 3-methylbutyric acid, pivalic acid, n-heptanoic acid, 2-methylhexanoic acid, n-octanoic acid, 2-ethylhexanoic acid, n-nonanoic acid, isononanoic acid, neononanoic acid, 3,5,5-trimethylhexanoic acid, n-decanoic acid, 2-propylheptanoic acid, neodecanoic acid or Versatic Acid 10, Versatic Acids 911, Versatic Acids 1519, lauric acid, tridecanoic acid, palmitic acid, stearic acid or benzoic acid or naphthalenecarboxylic acid.

However, it is also possible to transvinylate lower carboxylic acids, such as propionic acid, n-butyric acid, isobutyric acid, acrylic acid, crotonic acid or methacrylic acid, with vinyl acetate by the process according to the invention. Based on the molar carboxylic acid input, vinyl acetate is typically used in a molar excess of up to 10:1, preferably up to 5:1. The reaction mixture is typically worked up by distillation. Excess vinyl acetate, acetic acid formed, and the desired vinyl ester are drawn off as volatile components and separated further. In the residue, the starting carboxylic acid remains together with the transvinylation catalyst. The catalyst-containing residue is, after optimal discharge of a high boiler-containing substream, recycled back into the transvinylation reaction, optionally after addition of fresh catalyst or fresh ligands.

It is likewise possible to use vinyl acetate in a molar deficiency down to 0.1:1, preferably down to 0.2:1, based on the molar carboxylic acid input. This can reduce the level of complexity for removal of the vinyl acetate.

The transvinylation catalysts used are complexes of the transition metals from the platinum group, ruthenium, osmium, rhodium, iridium, palladium and platinum, which have been modified with mono- or polydentate organonitrogen or organophosphorus ligands. The total concentration of the transition metal(s) if a mixture thereof is used is generally from 0.005 to 1.5 mol %, preferably from 0.01 to 1.0 and especially from 0.02 to 0.6 mol %, based in each case on the starting compound used in deficiency, i.e. based on the carboxylic acid R—C(O)OH used or based on the transvinylating reagent $R^1C(O)O$—CH=CH$_2$ used. Even though it is possible to use the transition metal-ligand complex of stoichiometric composition as the catalyst, it is customary to work in the presence of excess ligands, i.e. ligand which has not entered into a complex bond with the transition metal. For each mole of transition metal, 1 to 40 and preferably 3 to 30 mol of ligand is employed. Particularly useful molar ratios of transition metal to ligand have been found to be within the range from 1:3 to 1:10. Suitable monodentate organonitrogen ligands are, for example, pyridine, quinoline, the positional picoline isomers, the positional lutidine isomers, collidine, aniline, the positional toluidine isomers, the positional xylidine isomers, N-methylaniline or aliphatic and aromatic amides such as N,N-dimethylformamide, acetanilide or N-methyl-2-pyrrolidone; suitable monodentate organophosphorus ligands are, for example, trialkylphosphines such as tributylphosphine or trioctylphosphine, triarylphosphines such as triphenylphosphine or tritolylphosphine, tricycloalkylphosphines such as tricyclohexylphosphine, alkylarylphosphines such as monobutyldiphenylphosphine or dipropylphenylphosphine, cycloalkylarylphosphines, trialkyl phosphites or triaryl phosphites such as triphenyl phosphite or trinaphthyl phosphite. Suitable polydentate organonitrogen or organophosphorus ligands are, for example, bidentate ligands such as 2,2'-bipyridyl, 1,10-phenanthroline, N,N,N',N'-tetramethylethylenediamine, P,P,P',P'-tetraphenyl-1,2-diphosphinoethane, 4,7-diphenyl-1,10-phenanthroline, 5-chloro-1,10-phenanthroline, 3,4,7,8-tetramethyl-1,10-phenanthroline, 2,9,4,7-tetramethyl-1,10-phenanthroline, 2,9-dimethyl-4,7-diphenyl-1,10-phenanthroline, 2,9-dimethyl-1,10-phenanthroline, 4,4'-diphenyl-2,2'-bipyridyl, 4-methyl-1,10-phenanthroline, 2,2'-biquinoline or 5-methyl-1,10-phenanthroline.

The transition metal-ligand complex need not be of homogeneous composition, but may consist, for example, of a mixture of transition metal-ligand complexes which differ in the nature of the ligands and/or of the transition metal. It is likewise possible for the free ligand present in the organic solution to be composed of a mixture of different mono- or polydentate organonitrogen or organophosphorus ligands. The transvinylation catalyst is typically formed from the transition metal, a transition metal compound or corresponding mixtures and the mono- or polydentate organonitrogen ligand, organophosphorus ligand or corresponding mixtures, under the conditions of the transvinylation reaction in the reaction mixture.

It is likewise possible to prepare the transvinylation catalyst separately in a preformation reaction. A suitable solvent in which the preformation is conducted may be the transvinylating reagent, the starting carboxylic acid to be vinylated or a mixture thereof. The conditions of the preformation step correspond generally to the conditions of the transvinylation reaction. The preformation conditions may be established on startup of the transvinylation process, such that the transvinylation reagent and the starting carboxylic acid to be vinylated are not admitted into the reaction vessel until the active transvinylation catalyst has formed in the initially charged organic solution. If the transition metal-ligand complex catalyst is added during the running process, a solution of the active transition metal-ligand complex catalyst should first be prepared in a separate preformation step, this subsequently being added to the process as a fresh solution. In this case, the solvent used in the preformation step is the transvinylating reagent, the starting carboxylic acid to be vinylated or a mixture thereof. During the preformation step too, the ligand can be used in excess, such that the aforementioned molar ratios between transition metal and ligand are established during the transvinylation reaction.

The transvinylation catalysts used may likewise be unmodified transition metal complexes containing at least one transition metal selected from the group of ruthenium, osmium, rhodium, iridium, palladium and platinum, which do not bear any mono- or polydentate organonitrogen or organophosphorus ligands. It can be assumed that, under the conditions of the transvinylation reaction, the active transition metal complex forms from the catalyst precursors used, such as the transition metals or transition metal carbonyls, carboxylates, halides or acetylacetonates. In the case of use of unmodified transition metal complexes, carbon monoxide is optionally added. Particularly ruthenium catalysts are used in unmodified form.

In the case of use of unmodified transition metal complexes, it may be found to be advantageous also to add a redox-active transition metal of group Ib of the periodic table of the elements and an alkali metal compound. An example of a suitable redox-active transition metal is copper, in the form of halides of divalent copper. The alkali metal compounds used are preferably lithium compounds, for example lithium carboxylates such as lithium acetate or lithium propionate, lithium carbonate, lithium hydrogencarbonate, lithium chloride or lithium hydroxide. A suitable transvinylation catalyst may be formed, for example, from the palladium chloride, copper(II) bromide and lithium acetate precursors. The active transvinylation catalyst is formed from the suitable precursors in the reaction vessel under the reaction conditions. Preformation of the catalyst, either at the start in the reaction vessel or in a separate vessel, is likewise possible.

The transition metal from the platinum group is used either in the form of a metal or in the form of a compound. In metallic form, it is used either in the form of finely divided particles or precipitated in a thin layer on a support, such as activated carbon, calcium carbonate, aluminium silicate, alumina. Suitable transition metal compounds are salts of the starting carboxylic acid to be vinylated, or salts of the corresponding carboxylic acid formed, for example acetates, propionates, butyrates, 2-ethylhexanoates or isononanoates. It is also possible to use salts of inorganic hydrogen or oxygen acids, such as nitrates or sulphates, the various oxides, or else carbonyl compounds or complexes such as cyclooctadienyl compounds or acetylacetonates. Transition metal-halogen compounds are possible, but are not as useful due to the corrosive behaviour of the halide ions.

Preference is given to using palladium or ruthenium compounds, especially the acetates, propionates, butyrates, 2-ethylhexanoates, isononanoates, acetylacetonates, triflates, trifluoroacetates or carbonyls thereof, such as $Ru_3(CO)_{12}$, $H_4Ru_4(CO)_{12}$ or $[Ru(CO)_2OAc]_n$.

The liquid output from the reaction vessel is subsequently decompressed to standard pressure via decompression stages and worked up in further separation devices. It may also be found to be appropriate first to cool the liquid reaction output to such a temperature that the formation of gaseous products in the decompression stage is reduced. Any gaseous components formed are removed, and the resulting liquid phase is worked up further. The liquid reaction mixture comprising the transvinylating reagent, the carboxylic acid formed, the desired vinyl ester, the starting carboxylic acid and the transvinylating catalyst is separated and split into the individual product streams, and transvinylating agent recovered is typically recycled back into the reaction vessel, and the carboxylic acid formed is removed from the process, and the desired vinyl ester is purified further. The transvinylating catalyst collects in the least volatile reaction component and is, optionally after discharge of a high boiler-containing substream, recycled into the reaction vessel. Depending on the physical properties of the reactants, the least volatile reaction component may, for example, be the unconverted starting carboxylic acid, the carboxylic acid formed or the transvinylating reagent. It is likewise possible to introduce the liquid output from the reaction vessel directly to a separating unit which is operated under pressure, and to further process the streams obtained separately.

In the case of vinyl acetate as the transvinylating reagent, it has been found to be appropriate to decompress the reaction mixture, to standard pressure and to work it up by distillation. Vinyl acetate, the acetic acid formed and the desired vinyl ester are separated as volatile components from the unconverted starting carboxylic acid comprising the transvinylation catalyst. The volatile components drawn off are subsequently separated by distillation into vinyl acetate, acetic acid and desired vinyl ester. Vinyl acetate is recycled into the reaction vessel, acetic acid is discharged, and the desired vinyl ester is purified further. The higher-boiling catalyst-containing starting carboxylic acid is recycled again as the catalyst circulation stream. Optionally, a high boiler-containing substream is withdrawn from the catalyst circuit, and fresh catalyst is added, optionally in preformed form, or only fresh ligand.

The preferred process according to the invention is explained in detail hereinafter, with reference to the flow diagram according to the FIGURE, for the case in which the starting carboxylic acid is the least volatile and is obtained as a less volatile residue in the workup of the reaction mixture. The process according to the invention, however, is not limited to the embodiment shown in the drawing and can also be applied successfully to those embodiments in which any reactant is obtained as a less volatile component.

The transvinylating reagent $R^1$—C(O)—CH=$CH_2$ is conducted via line (1), and the starting carboxylic acid R—C(O)OH to be vinylated via line (2), into a mixing vessel (3) from which the mixture is introduced via line (4) into the reaction vessel (5). The liquid reaction output is introduced via line (6) to a decompression vessel (7) in which it is decompressed to standard pressure. Optionally, the liquid reaction output is first passed into a cooling device (7') (shown with dotted lines) and introduced in cooled form via line (6) to the decompression vessel (7), in order to keep all components liquid in the course of decompression. Any gas phase formed is removed via line (8), and the liquid phase formed is introduced via line (9) to the separating vessel (10). In the separating vessel (10), splitting is effected into a volatile fraction enriched with the transvinylating reagent $R^1$—C(O)O—CH=CH$_2$, the carboxylic acid $R^1$—C(O)OH formed, and the desired vinyl ester R—C(O)O—CH=CH$_2$, which is combined via line (11) with any volatile components from the decompression stage conducted in via line (8), and conducted via line (12) to the separating vessel (13). The transvinylating reagent removed in the separating vessel (13) is recycled via line (14) and combined with the transvinylating reagent $R^1$—C(O)O—CH=CH$_2$ conducted in via line (1). The carboxylic acid $R^1$—C(O)OH which is formed during the transvinylation reaction and obtained in the separating vessel (13), and the desired vinyl ester R—C(O)O—CH=CH$_2$, are removed via line (15) and introduced to the separating vessel (16), from which the carboxylic acid $R^1$—C(O)OH formed flows out via line (17) and the desired vinyl ester R—C(O)O—CH=CH$_2$ via line (18). The vinyl ester obtained via line (18) can be subjected to a further fine purification (not shown in the FIGURE).

The less volatile fraction obtained in the separating vessel (10), which in a preferred embodiment comprises the unconverted starting carboxylic acid R—C(O)OH and the transvinylation catalyst, is removed via line (19) and, optionally after discharging a high boiler-containing side stream, recycled via line (20) (shown as a dotted line) as a catalyst circulation stream via line (21). Optionally, fresh catalyst, optionally in preformed form, or fresh ligand is added via line (22) (shown as a dotted line) to the catalyst circulation stream, and the mixture of used and fresh catalyst is fed via line (23) into the mixing vessel (3). Both in the reaction section and in the workup section, inhibitor can be added at suitable points (not shown in the FIGURE). Suitable separating vessels (10), (13) and (16) are apparatus customary for separating operations, such as thin-film evaporators, short-path evaporators or distillation columns. The temperature and pressure conditions to be established are guided by the components present in the reaction mixture for workup and can be determined by routine tests. The design of the separating vessels, such as the necessity for and number of separating plates, can likewise be determined by routine tests or simulation.

The invention is illustrated in detail in the examples which follow, but is not limited to the embodiments described.

EXAMPLES

For the performance of the examples which follow, the experimental setup according to the FIGURE was used. In the reservoir vessel (3), vinyl acetate (examples 1-7, 15-22) or vinyl propionate (Examples 8-14) conducted in via line (1), the starting carboxylic acid R—C(O)OH to be vinylated via line (2), and catalyst solution via line (23) were mixed and pumped via line (4) to the reaction vessel (5) configured as a flow tube. The liquid reaction mixture withdrawn via line (6) was decompressed to standard pressure in the decompression vessel (7). Gaseous components formed, which comprised vinyl acetate or vinyl propionate and acetic acid or propionic acid formed, were drawn off via line (8). The liquid output removed via line (9) was analysed by gas chromatography.

The starting carboxylic acids R—C(O)OH used for transvinylation, the reaction conditions established in the reaction vessel (5) and the space-time yields of the desired vinyl esters R—C(O)O—CH=CH$_2$ determined in the gas chromatography analysis are compiled in Tables 1 to 7 below. The catalyst solution was prepared by blending the palladium acetate Pd(OAc)$_2$ catalyst precursor with the bidentate nitrogen ligands 1,10-phenanthroline (Examples 1-16, 21-24) or 2,2'-bipyridyl (Examples 17, 18) in a mixture of vinyl acetate or vinyl propionate and the respective starting carboxylic acid. In Examples 19 and 20, the [Ru(CO)$_2$OAc]$_n$ complex was used as the catalyst precursor. In Examples 21-23, based on the molar carboxylic acid input, vinyl acetate was used in a molar deficiency. The active catalyst was formed in the reaction vessel under reaction conditions. The molar ratio stated for the catalyst precursor is based on mol of palladium or mol of ruthenium. The isononanoic acid used was based on the hydroformylation of diisobutylene with subsequent oxidation of the corresponding aldehyde and contained predominantly 3,5,5-trimethylhexanoic acid.

TABLE 1

Conditions and results of the continuous preparation of vinyl esters in a flow tube with vinyl acetate as the transvinylating reagent at elevated pressure (Pd(OAc)$_2$/1,10-phenanthroline)

| Example No. | 1 | 2 | 3 | 4 | 5 | 6 | 7 |
|---|---|---|---|---|---|---|---|
| Carboxylic acid R—C(O)OH | Isononanoic acid (3,5,5-trimethyl-hexanoic acid) | Benzoic acid | Pivalic acid | Neodecanoic acid | 2-Ethyl-hexanoic acid | Heptanoic acid | Lauric acid |
| Residence time [min] | 75 | 75 | 75 | 75 | 75 | 75 | 75 |
| Reactor volume [ml] | 100 | 100 | 100 | 100 | 100 | 100 | 100 |
| Temperature [° C.] | 140 | 140 | 140 | 140 | 140 | 140 | 140 |
| Pressure [MPa] | 2 | 2 | 2 | 2 | 2 | 2 | 2 |
| Molar ratio of carboxylic acid:vinyl acetate:catalyst precursor | 1.0:5.0:0.0010 | 1.0:8.0:0.0010 | 1.0:5.0:0.0010 | 1.0:5.0:0.0010 | 1.0:5.0:0.0010 | 1.0:5.0:0.0010 | 1.0:8.0:0.0010 |
| Molar ratio of catalyst precursor:ligand | 1:8 | 1:8 | 1:8 | 1:8 | 1:8 | 1:8 | 1:8 |
| Catalyst precursor | Pd(OAc)$_2$ | Pd(OAc)$_2$ | Pd(OAc)$_2$ | Pd(OAc)$_2$ | Pd(OAc)$_2$ | Pd(OAc)$_2$ | Pd(OAc)$_2$ |
| Ligand | 1,10-phenanthroline | 1,10-phenanthroline | 1,10-phenanthroline | 1,10-phenanthroline | 1,10-phenanthroline | 1,10-phenanthroline | 1,10-phenanthroline |
| Carboxylic acid [g/h] | 19.8 | 11.7 | 14.2 | 23.4 | 18.5 | 17.2 | 16.6 |
| Vinyl acetate [g/h] | 53.9 | 65.8 | 59.9 | 58.4 | 55.4 | 57.0 | 56.9 |
| Catalyst precursor [mg/h] | 28.1 | 21.5 | 31.2 | 30.5 | 28.9 | 29.7 | 18.5 |
| Ligand [mg/h] | 180.6 | 137.8 | 200.6 | 195.6 | 185.4 | 190.8 | 119.1 |

TABLE 1-continued

Conditions and results of the continuous preparation of vinyl esters in a flow tube with vinyl acetate as the transvinylating reagent at elevated pressure (Pd(OAc)$_2$/1,10-phenanthroline)

| Example No. | 1 | 2 | 3 | 4 | 5 | 6 | 7 |
|---|---|---|---|---|---|---|---|
| Conversion [%] | 83 | 86 | 81 | 72 | 82 | 80 | 74 |
| Yield [%] | 80 | 81 | 74 | 65 | 77 | 76 | 68 |
| Selectivity [%] | 97.0 | 94.4 | 91.3 | 89.9 | 93.5 | 95.0 | 91.9 |
| Space-time yield [g/l · h] | 185 | 115 | 132 | 175 | 168 | 157 | 128 |

TABLE 2

Conditions and results of the continuous preparation of vinyl esters in a flow tube with vinyl propionate as the transvinylating reagent at elevated pressure (Pd(OAc)$_2$/1,10-phenanthroline)

| Example No. | 8 | 9 | 10 | 11 | 12 | 13 | 14 |
|---|---|---|---|---|---|---|---|
| Carboxylic acid R—C(O)OH | Isononanoic acid (3,5,5-trimethyl-hexanoic acid) | Benzoic acid | Pivalic acid | Neodecanoic acid | 2-Ethyl-hexanoic acid | Heptanoic acid | Lauric acid |
| Residence time [min] | 75 | 75 | 75 | 75 | 75 | 75 | 75 |
| Reactor volume [ml] | 100 | 100 | 100 | 100 | 100 | 100 | 100 |
| Temperature [° C.] | 140 | 140 | 140 | 140 | 140 | 140 | 140 |
| Pressure [MPa] | 2 | 2 | 2 | 2 | 2 | 2 | 2 |
| Molar ratio of carboxylic acid:vinyl propionate:catalyst precursor | 1.0:5.0:0.0010 | 1.0:8.0:0.0010 | 1.0:5.0:0.0010 | 1.0:5.0:0.0010 | 1.0:5.0:0.0010 | 1.0:5.0:0.0010 | 1.0:8.0:0.0010 |
| Molar ratio of catalyst precursor:ligand | 1:8 | 1:8 | 1:8 | 1:8 | 1:8 | 1:8 | 1:8 |
| Catalyst precursor | Pd(OAc)$_2$ | Pd(OAc)$_2$ | Pd(OAc)$_2$ | Pd(OAc)$_2$ | Pd(OAc)$_2$ | Pd(OAc)$_2$ | Pd(OAc)$_2$ |
| Ligand | 1,10-phenanthroline | 1,10-phenanthroline | 1,10-phenanthroline | 1,10-phenanthroline | 1,10-phenanthroline | 1,10-phenanthroline | 1,10-phenanthroline |
| Carboxylic acid [g/h] | 17.6 | 10.1 | 12.4 | 18.8 | 16.4 | 15.2 | 14.6 |
| Vinyl propionate [g/h] | 55.6 | 66.3 | 61.0 | 54.6 | 57.0 | 58.4 | 58.3 |
| Catalyst precursor [mg/h] | 24.9 | 18.6 | 27.4 | 24.5 | 25.6 | 26.2 | 16.4 |
| Ligand [mg/h] | 160.2 | 119.3 | 175.7 | 157.3 | 164.1 | 168.2 | 105.0 |
| Conversion [%] | 80 | 82 | 77 | 69 | 79 | 76 | 69 |
| Yield [%] | 77 | 77 | 71 | 61 | 75 | 72 | 63 |
| Selectivity [%] | 96.1 | 93.9 | 92.2 | 88.4 | 94.9 | 94.7 | 91.3 |
| Space-time yield [g/l · h] | 158 | 94 | 110 | 132 | 145 | 131 | 104 |

TABLE 3

Conditions and results of the continuous preparation of vinyl esters in a flow tube with vinyl acetate as the transvinylating reagent at standard pressure (Pd(OAc)$_2$/1,10-phenanthroline)

| Example No. | 15 (Comparison) | 16 (Comparison) |
|---|---|---|
| Carboxylic acid R—C(O)OH | Isononanoic acid (3,5,5-trimethyl-hexanoic acid) | 2-Ethylhexanoic acid |
| Residence time [min] | 75 | 75 |
| Reactor volume [ml] | 100 | 100 |
| Temperature [° C.] | 140 | 140 |
| Pressure [MPa] | standard pressure | standard pressure |
| Molar ratio of carboxylic acid:vinyl acetate:catalyst precursor | 1.0:5.0:0.0010 | 1.0:5.0:0.0010 |
| Molar ratio of catalyst precursor:ligand | 1:8 | 1:8 |
| Catalyst precursor | Pd(OAc)$_2$ | Pd(OAc)$_2$ |
| Ligand | 1,10-phenanthroline | 1,10-phenanthroline |
| Carboxylic acid [g/h] | 19.8 | 18.5 |
| Vinyl acetate [g/h] | 53.9 | 55.4 |
| Catalyst precursor [mg/h] | 28.1 | 28.9 |
| Ligand [mg/h] | 180.6 | 185.4 |
| Conversion [%] | 75 | 79 |
| Yield [%] | 72 | 65 |
| Selectivity [%] | 96.5 | 82.7 |
| Space-time yield [g/l · h] | 167 | 143 |

TABLE 4

Conditions and results of the continuous preparation of vinyl esters in a flow tube with vinyl acetate as the transvinylating reagent at elevated pressure (Pd(OAc)$_2$/2,2'-bipyridyl)

| Example No. | 17 | 18 |
|---|---|---|
| Carboxylic acid R—C(O)OH | Isononanoic acid (3,5,5-trimethyl-hexanoic acid) | 2-Ethylhexanoic acid |
| Residence time [min] | 75 | 75 |
| Reactor volume [ml] | 100 | 100 |
| Temperature [° C.] | 140 | 140 |
| Pressure [MPa] | 2 | 2 |
| Molar ratio of carboxylic acid:vinyl acetate:catalyst precursor | 1.0:5.0:0.0010 | 1.0:5.0:0.0010 |
| Molar ratio of catalyst precursor:ligand | 1:8 | 1:8 |
| Catalyst precursor | Pd(OAc)$_2$ | Pd(OAc)$_2$ |
| Ligand | 2,2'-bipyridyl | 2,2'-bipyridyl |
| Carboxylic acid [g/h] | 19.8 | 18.5 |
| Vinyl acetate [g/h] | 53.9 | 55.4 |
| Catalyst precursor [mg/h] | 28.1 | 28.9 |
| Ligand [mg/h] | 156.5 | 160.7 |
| Conversion [%] | 64 | 67 |
| Yield [%] | 63 | 60 |
| Selectivity [%] | 97.3 | 89.8 |
| Space-time yield [g/l · h] | 144 | 131 |

TABLE 5

Conditions and results of the continuous preparation of vinyl esters in a flow tube with vinyl acetate as the transvinylating reagent at elevated pressure ([Ru(CO)$_2$OAc]$_n$)

| Example No. | 19 | 20 |
|---|---|---|
| Carboxylic acid R—C(O)OH | Isononanoic acid (3,5,5-trimethyl-hexanoic acid) | 2-Ethylhexanoic acid |
| Residence time [min] | 75 | 75 |
| Reactor volume [ml] | 100 | 100 |
| Temperature [° C.] | 140 | 140 |
| Pressure [MPa] | 2 | 2 |
| Molar ratio of carboxylic acid:vinyl acetate:catalyst precursor | 1.0:5.0:0.0010 | 1.0:5.0:0.0010 |
| Catalyst precursor | [Ru(CO)$_2$OAc]$_n$ | [Ru(CO)$_2$OAc]$_n$ |
| Carboxylic acid [g/h] | 19.8 | 18.5 |
| Vinyl acetate [g/h] | 53.9 | 55.4 |
| Catalyst precursor [mg/h] | 27.1 | 27.8 |
| Ligand [mg/h] | — | — |
| Conversion [%] | 28 | 38 |
| Yield [%] | 27 | 32 |
| Selectivity [%] | 94.8 | 84.7 |
| Space-time yield [g/l · h] | 61 | 70 |

TABLE 6

Conditions and results of the continuous preparation of vinyl esters in a flow tube with vinyl acetate as the transvinylating reagent and use of the starting carboxylic acid in excess at elevated pressure (Pd(OAc)$_2$/1,10-phenanthroline)

| Example No. | 21 | 22 |
|---|---|---|
| Carboxylic acid R—C(O)—OH | Isononanoic acid (3,5,5-trimethyl-hexanoic acid) | 2-Ethylhexanoic acid |
| Residence time [min] | 75 | 75 |
| Reactor volume [ml] | 100 | 100 |
| Temperature [° C.] | 140 | 140 |
| Pressure [MPa] | 2 | 2 |
| Molar ratio of carboxylic acid:vinyl acetate:catalyst precursor | 1.0:0.2:0.001 | 1.0:0.2:0.001 |
| Molar ratio of catalyst precursor:ligand | 1:8 | 1:8 |
| Catalyst precursor | Pd(OAc)$_2$ | Pd(OAc)$_2$ |
| Ligand | 1,10-phenanthroline | 1,10-phenanthroline |
| Carboxylic acid [g/h] | 65.1 | 65.0 |
| Vinyl acetate [g/h] | 7.1 | 7.8 |
| Catalyst precursor [g/h] | 0.0924 | 0.1012 |
| Ligand [g/h] | 0.5935 | 0.6497 |
| Conversion [%] [a] | 19 | 18 |
| Yield [%] [a] | 18 | 17 |
| Selectivity [%] | 96.3 | 94.4 |
| Space-time yield [g/l · h] | 139 | 141 |

[a] based on input of carboxylic acid R—C(O)—OH

TABLE 7

Conditions and results of the continuous preparation of vinyl esters in a flow tube with vinyl acetate as the transvinylating reagent and employing residence times of less than 1 h at elevated pressure (Pd(OAc)$_2$/1,10-phenanthroline)

| Example No. | 23 | 24 |
|---|---|---|
| Carboxylic acid R—C(O)—OH | Isononanoic acid (3,5,5-trimethyl-hexanoic acid) | Isononanoic acid (3,5,5-trimethyl-hexanoic acid) |
| Residence time [min] | 11 | 11 |
| Reactor volume [ml] | 200 | 200 |
| Temperature [° C.] | 150 | 140 |
| Pressure [MPa] | 2 | 2 |
| Molar ratio of carboxylic acid:vinyl acetate:catalyst precursor | 1.00:0.33:0.00165 | 1.00:5.00:0.002 |
| Molar ratio of catalyst precursor:ligand | 1:5 | 1:8 |
| Catalyst precursor | Pd(OAc)$_2$ | Pd(OAc)$_2$ |
| Ligand | 1,10-phenanthroline | 1,10-phenanthroline |
| Carboxylic acid [g/h] | 838.2 | 263.7 |
| Vinyl acetate [g/h] | 150.5 | 717.4 |
| Catalyst precursor [g/h] | 1.9621 | 0.7483 |
| Ligand [g/h] | 7.8752 | 4.8051 |
| Conversion [%] [a] | 25 | 75 |
| Yield [%] [a] | 24 | 74 |
| Selectivity [%] | 97.8 | 98.5 |
| Space-time yield [g/l · h] | 1193 | 1134 |

[a] based on input of carboxylic acid R—C(O)—OH

As the results in Tables 1, 2, 4 and 5 show, very high space-time yields are achieved in the transvinylation reaction operated continuously in the steady state, these being unachievable in the known processes for reactive distillation with continuous removal of vinyl acetate and acetic acid from the reaction. Moreover, the known processes require a high vinyl acetate input, since a large amount of vinyl acetate has to be used in the reactive distillation and a large reaction volume is covered.

It is likewise possible, as shown by the results compiled in Table 3, also to achieve a high space-time yield in the case of a reaction regime under standard pressure. Also in the case of a reaction regime in which vinyl acetate is used in a molar deficiency, it is possible to obtain high space-time yields of the desired vinyl ester (Table 6). According to Table 7, the residence times in the flow tube can be adjusted to less than 1 hour, such that it is possible to establish states of operation with high load which enable a distinct rise in the space-time yield.

The crude product obtained in the decompression vessel (7) was introduced via line (9) to a thin-film evaporator (10), from which, at a shell temperature of 95° C. and under reduced pressure, the top product comprising vinyl acetate or vinyl propionate, acetic acid or propionic acid and the respective vinyl ester R—C(O)O—CH=CH$_2$ was drawn off. This product stream was combined with the gaseous components from the decompression vessel (7) and conducted via line (12) to the distillation column (13), in which the product mixture was split into a top fraction composed of vinyl acetate or vinyl propionate and into a bottom product composed of acetic acid or propionic acid and the respective vinyl ester R—C(O)O—CH=CH$_2$. The vinyl acetate- or vinyl propionate-containing stream was recycled via line (14) and the bottom product was introduced via line (15) to a further distillation column (16) in which acetic acid or propionic acid was drawn off as the top product. The bottom product obtained via line (18) was the respective vinyl ester R—C(O)O—CH=CH$_2$. The respective distillation conditions in the thin-film evaporator (10) and in the distillation columns (13) and (16) could be established by routine optimization.

From the liquid output of the thin-film evaporator (10), based on 100 parts by mass, about 5-10 parts by mass of a high boiler-containing side stream were discharged via line (20), while the remainder was recycled as a catalyst circulation stream. Via line (22), fresh catalyst was added, according to the ratios to be established in the flow tube (5). The fresh catalyst was added in solution, by introducing palladium acetate and 1,10-phenanthroline or 2,2'-bipyridyl or [Ru(CO)$_2$OAc]$_n$ in a mixture of vinyl acetate or vinyl propionate and the respective starting carboxylic acid.

The invention claimed is:

1. Continuous, catalytic process for preparing a vinyl ester of the formula R—C(O)O—CH=CH$_2$ by reaction of a carboxylic acid of the formula R—C(O)OH with a transvinylating reagent of the formula R$^1$—C(O)O—CH=CH$_2$ where R and R$^1$ are each independently an aliphatic, cycloaliphatic or aromatic radical, characterized in that the reaction is effected at a temperature of 90 to 160° C. and at a pressure of 0.8 to 8 MPa without withdrawal of a reactant such that the reaction system is in the steady state, the reaction also being effected in the presence of a transition metal catalyst containing at least one transition metal from the group of ruthenium, osmium, rhodium, iridium, palladium and platinum, and then the resulting reaction mixture is separated into its constituents.

2. Process according to claim 1, characterized in that the reaction is conducted at a temperature of 90 to 150° C.

3. Process according to claim 1, characterized in that the reaction is conducted at a pressure of 0.8 to 2 MPa and at a temperature of 90 to 140° C.

4. Process according to claim 1, characterized in that the R radical in the carboxylic acid of the formula R—C(O)OH contains 2 to 20 carbon atoms.

5. Process according to claim 4, characterized in that the carboxylic acid of the formula R—C(O)OH is selected from the group of propionic acid, n-butyric acid, isobutyric acid, n-valeric acid, 2-methylbutyric acid, 3-methylbutyric acid, pivalic acid, n-heptanoic acid, 2-methylhexanoic acid, 2-ethylhexanoic acid, n-octanoic acid, n-nonanoic acid, isononanoic acid, neononanoic acid, 3,5,5-trimethylhexanoic acid, n-decanoic acid, 2-propylheptanoic acid, neodecanoic acid, a mixture of isomeric C9 to C11 acids, a mixture of isomeric C15 to C19 acids, lauric acid, tridecanoic acid, palmitic acid, stearic acid, benzoic acid, naphthalenecarboxylic acid, acrylic acid, crotonic acid and methacrylic acid.

6. Process according to claim 1, characterized in that the R$^1$ radical in the transvinylating reagent of the formula R$^1$—C(O)O—CH=CH$_2$ contains 1 to 20 carbon atoms.

7. Process according to claim 6, characterized in that R$^1$ is methyl, ethyl or undecyl.

8. Process according to claim 1, characterized in that the transition metal catalyst contains mono- or polydentate organonitrogen or organophosphorus ligands in complexed form.

9. Process according to claim 1, characterized in that the total concentration of the transition metal(s) is 0.005 to 1.5 mol %, based on the starting compound used in deficiency.

10. Process according to claim 8, characterized in that a molar ratio of transition metal to mono- or polydentate organonitrogen or organophosphorus ligands is from 1:1 to 1:40.

11. Process according to claim 8, characterized in that the transition metal used is palladium and the polydentate organonitrogen ligand used is 1,10-phenanthroline or 2,2'-bipyridyl.

12. Process according to claim 1, characterized in that the transition metal catalyst additionally contains a redox-active transition metal from group Ib of the periodic table of the elements and an alkali metal compound.

13. Process according to claim 12, characterized in that, as well as the transition metal, copper is additionally used as a redox-active transition metal from group I of the periodic table of the elements, and a lithium compound selected from the group of lithium carboxylates, lithium carbonate, lithium hydrogencarbonate, lithium chloride and lithium hydroxide is used as an alkali metal compound.

14. Process according to claim 13, characterized in that the transition metal used is palladium.

15. Process according to claim 1, characterized in that the reaction is effected in a tubular reactor.

16. Process according to claim 15, characterized in that the tubular reactor is provided with a circulation pump and optionally with a heat exchanger.

17. Process according to claim 1, characterized in that the reaction is effected at a pressure of 0.8 to 2 MPa.

18. Process according to claim 1, characterized in that the total concentration of the transition metal(s) is 0.01 to 1 mol %, based on the starting compound used in deficiency.

19. Process according to claim 10, characterized in that the molar ratio of transition metal to mono- or polydentate organonitrogen or organophosphorus ligands is from 1:3 to 1:30.

* * * * *